(12) United States Patent
Mitachi et al.

(10) Patent No.: US 7,574,893 B2
(45) Date of Patent: Aug. 18, 2009

(54) ODOR SENSOR

(75) Inventors: Seiko Mitachi, Hachioji (JP); Toshio Matsunaga, Hachioji (JP)

(73) Assignees: Katayanagi Institute, Tokyo (JP); Seiko Mitachi, Tokyo (JP)

( * ) Notice: Subject to any disclaimer, the term of this patent is extended or adjusted under 35 U.S.C. 154(b) by 269 days.

(21) Appl. No.: 10/573,896

(22) PCT Filed: May 24, 2005

(86) PCT No.: PCT/JP2005/009444

§ 371 (c)(1),
(2), (4) Date: Nov. 20, 2006

(87) PCT Pub. No.: WO2005/114157

PCT Pub. Date: Dec. 1, 2005

(65) Prior Publication Data

US 2007/0151324 A1    Jul. 5, 2007

(30) Foreign Application Priority Data

May 24, 2004    (JP)    ............................. 2004-153744

(51) Int. Cl.
*G01N 7/00* (2006.01)
(52) U.S. Cl. .................................... 73/23.34
(58) Field of Classification Search ................. 73/23.34
See application file for complete search history.

(56) References Cited

FOREIGN PATENT DOCUMENTS

| JP | 1-259250 A | 10/1989 |
|----|------------|---------|
| JP | 7-12767 A  | 1/1995  |

OTHER PUBLICATIONS

Hiroshi Asai, "Odor Detector," Solid state Physics (Kotai Butsuri in Japanese), 10(7):369-373 (1975).

K. Iriyama et al., Olefactory Biophysical Chemistry—Effect of Gas Adsorption on the Electric Conductivity of Amorphous Thin Films of β-Carotene and Oxidized β-Carotene-, Jikeikai Medical Jounsal, 37(3):299-310 (1990).

Mitachi et al., "Selection of Optimal Desiccants for Use in Ordor Sensors," The 50th Spring Meeting of Japan Society of Applied Physics and Related Societies, 29:B-13 (Mar. 29, 2003).

*Primary Examiner*—Hezron Williams
*Assistant Examiner*—Rodney T Frank
(74) *Attorney, Agent, or Firm*—Finnegan, Henderson, Farabow, Garrett & Dunner, LLP

(57) ABSTRACT

The present invention provides a biomimetic odor sensor that utilizes neither an oxide semiconductor nor a quartz oscillator, is hardly affected by the atmospheric moisture, simple in structure, inexpensive in production cost, fast in reaction rate, of a wet type, and provided with the condition close to the condition of the nasal mucosa of the human olfactus organ. The sensor 10 according to the present invention includes a mixed material 12 in which β-carotene and a reducing agent to prevent the oxidation of the β-carotene are dispersed in a viscous liquid, and a cathode electrode 16 and an anode electrode 18 are disposed so as to be in contact with the mixed material 12.

11 Claims, 19 Drawing Sheets

FIG.15

| FIG.15A |
| FIG.15B |
| FIG.15C |

COMPARISON OF THE PRESENT METHOD WITH CONVENTIONAL METHODS

| | CONDITION OF β-CAROTENE | MEASUREMENT METHOD | CURRENT VARIATION RANGE (A) | RESPONSE RATE | REACTANT | CURRENT PEAK VALUE |
|---|---|---|---|---|---|---|
| ROSENBERG | β POWDER TYPE (DRY TYPE) | SANDWICHING WITH TWO SHEETS OF ELECTRODES | 10-12 ~ 10-6 | 1 h | METHANOL | 1 μA |
| ASAI | DISSOLVED IN PETROLEUM ETHER (EVENTUALLY, DRY TYPE) | COATING ON QUARTZ OR GLASS PLATE, THIN FILM | 10-9 ~ 10-6 | 0.4 h | METHANOL | 10 μA |
| MITACHI LAB EXAMPLE 1 | GLYCERIN + SODIUM THIOSULFATE + ETHANOL (WET TYPE) | SANDWICHING WITH COPPER PLATE AND STAINLESS-STEEL MESH | 10-3 ~ 10-2 | < 1 min | AMMONIA | 18 mA |

FIG.15A

| | | | | |
|---|---|---|---|---|
| MITACHI LAB EXAMPLE 7 | GLYCERIN + SODIUM THIOSULFATE + ETHANOL (WET TYPE) | SANDWICHING WITH PLATINUM PLATE AND STAINLESS-STEEL MESH | 0.2 ~ 0.3 | < 1 min | AMMONIA | 300 mA |
| MITACHI LAB EXAMPLE 2 | GLYCERIN + SODIUM THIOSULFATE + ETHANOL (WET TYPE) | SANDWICHING WITH COPPER PLATE AND STAINLESS-STEEL MESH | | 2 min | TRIMETHYL AMINE | 50 μA |
| MITACHI LAB EXAMPLE 3 | GLYCERIN + SODIUM THIOSULFATE + ETHANOL (WET TYPE) | SANDWICHING WITH COPPER PLATE AND STAINLESS-STEEL MESH | | 40 sec | BUTANOL | 23 μA |
| MITACHI LAB EXAMPLE 4 | GLYCERIN + SODIUM THIOSULFATE + ETHANOL (WET TYPE) | SANDWICHING WITH PLATINUM PLATE AND STAINLESS-STEEL MESH | | 15 min 14 sec | PROPANOL | 133 μA |
| MITACHI LAB | GLYCERIN + SODIUM THIOSULFATE + ETHANOL (WET TYPE) | SANDWICHING WITH COPPER PLATE AND STAINLESS-STEEL MESH | | 8 min | METHANOL | 600 μA |
| MITACHI LAB | GLYCERIN + SODIUM THIOSULFATE + ETHANOL (WET TYPE) | SANDWICHING WITH COPPER PLATE AND STAINLESS-STEEL MESH | | 13 min | ACETONE | 110 μA |
| MITACHI LAB | GLYCERIN + SODIUM THIOSULFATE + ETHANOL (WET TYPE) | SANDWICHING WITH COPPER PLATE AND STAINLESS-STEEL MESH | | 13 min 55 sec | BENZENE | 34 μA |
| MITACHI LAB EXAMPLE 5 | GLYCERIN + SODIUM THIOSULFATE + ETHANOL (WET TYPE) | SANDWICHING WITH COPPER PLATE AND STAINLESS-STEEL MESH | | 2 min 55 sec | 2-PHENYL ETHANOL | 1.62 mA |

FIG.15B

| | | | |
|---|---|---|---|
| MITACHI LAB EXAMPLE 6 | GLYCERIN + SODIUM THIOSULFATE + ETHANOL (WET TYPE) | SANDWICHING WITH COPPER PLATE AND STAINLESS-STEEL MESH | 5 min 37 sec | GERANIOL | 85 μA |
| MITACHI LAB | GLYCERIN + SODIUM THIOSULFATE + ETHANOL (WET TYPE) | SANDWICHING WITH COPPER PLATE AND STAINLESS-STEEL MESH | 25 min 35 sec | CITRONELLOL | 1.2 mA |
| MITACHI LAB | GLYCERIN + SODIUM THIOSULFATE + ETHANOL (WET TYPE) | SANDWICHING WITH COPPER PLATE AND STAINLESS-STEEL MESH | 1 h | ALPHA-PINENE | 240 mA |
| MITACHI LAB | GLYCERIN + SODIUM THIOSULFATE + ETHANOL (WET TYPE) | SANDWICHING WITH COPPER PLATE AND STAINLESS-STEEL MESH | 20 min 55 sec | HEATED COOKING OIL | 2.2 mA |

FIG.15C

ODOR SENSOR

TECHNICAL FIELD

The present invention relates to an odor sensor that is of a wet type and detects odor with the condition to model after the condition of the nasal mucosa of the human olfactus organ.

BACKGROUND ART

Rosenberg et al. established in 1961 that when a microcrystalline powder of β-carotene is sandwiched between 2 sheets of electrodes, and the electric conductivity of the powder of β-carotene is measured in various gases, the electric conductivity of the powder of β-carotene is remarkably increased in gases that are sensed by us as odor such as ethanol, ammonia or acetone (for example, see Non-Patent Document 1).

Generally, oxide semiconductor odor sensors that utilize oxide semiconductors are known. An oxide semiconductor odor sensor is a device that utilizes a mechanism to detect the variation of the resistance value of the semiconductor caused by the adsorption/reaction of odor molecules on the surface of the semiconductor. Among oxide semiconductor odor sensors, some oxide semiconductor odor sensors have been developed in such a way that the oxide semiconductors are heated with a heater at high temperatures (about 500° C.) to eliminate the effects of the ambient temperature/humidity; however, such sensors are complex in structure, can hardly be reduced in size, and is high in production cost.

Additionally known are quartz oscillator odor sensors that utilize the mechanism of the variation of the resonant frequency of the quartz oscillator caused by the adsorption of odor molecules on the quartz oscillator.

Non-Patent Document 1: Hiroshi Asai, "Odor Detectors," Solid State Physics (Kotai Butsuri in Japanese), Vol. 10, No. 7, pp. 369-373 (1975).

Non-Patent Document 2: Mitachi, Kondo, Sasaki, and Sugimoto, "Selection of Optimal Desiccants for Use in Odor Sensors," The 50th Spring Meeting of Japan Society of Applied Physics and Related Societies, 29p-B-13 (Mar. 29, 2003).

DISCLOSURE OF THE INVENTION

However, as shown in FIG. 1, an odor sensor utilizing a microcrystalline powder of β-carotene is slow in reaction rate (about 40 minutes), and the generated current is as weak as 10 μA or less, so that it is far from practical use. Additionally, β-carotene tends to be easily oxidized, leading to a drawback that such a sensor cannot stand long-term use.

In an oxide semiconductor odor sensor utilizing an oxide semiconductor needs, as described above, a device for heating the oxide semiconductor with a heater at high temperatures (about 500° C.), leading to a drawback that such a sensor is complex in structure, can hardly be reduced in size, and high in production cost.

A quartz oscillator odor sensor has a drawback that it also responds to the atmospheric moisture, and accordingly needs a heater for use at high temperatures or a desiccant (for example, see Non-Patent Document No. 2). Such a sensor also needs a device for inducing oscillation on a steady basis, leading to a drawback that such a sensor can hardly be reduced in size and is high in production cost.

The present invention has been achieved in view of the above described problems, and an object of the present invention is to provide a biomimetic odor sensor that utilizes neither an oxide semiconductor nor a quartz oscillator, is hardly affected by the atmospheric moisture, in other words, does not need a heater, is simple in structure, inexpensive in production cost, fast in reaction rate, of a wet type, and provided with the condition close to the condition of the nasal mucosa of the human olfactus organ.

For the purpose of achieving such an object, a first aspect of the present invention is characterized by including a mixed material in which β-carotene and a reducing agent to prevent the oxidation of the β-carotene are dispersed in a viscous liquid, and a cathode electrode and an anode electrode are disposed so as to be in contact with the mixed material. This construction makes it possible to provide a biomimetic odor sensor that is of a wet type and provided with the condition close to the condition of the nasal mucosa of human olfactus organ. The use of a biomimetic sensor based on this construction makes it possible to provide a sensor that reacts fast to various odors.

A second aspect of the present invention is characterized in that the reducing agent is any one of the following reducing agents: sodium thiosulfate ($Na_2S_2O_3$), hydro nicotinamide adenine dinucleotide phosphate (NADPH), $Na_2(H_2PO_2)$ and L-ascorbic acid. This construction can suppress the degradation of the sensor due to the oxidation of β-carotene and makes it possible to provide an odor sensor that can stand long-term use.

A third aspect of the present invention is characterized in that the viscous liquid is a liquid with high viscosity and polarity.

A fourth aspect of the present invention is characterized in that the liquid with high viscosity and polarity is glycerin. This construction makes it possible to provide an odor sensor that is inexpensive in production cost.

A fifth aspect of the present invention is characterized in that ethanol is further mixed as a viscosity modifier. This makes it possible to provide an odor sensor that is fast in reaction rate while the viscosity is being modified.

A sixth aspect of the present invention is characterized by having a structure in which the cathode electrode and the anode electrode are made to face each other so as to sandwich the mixed material.

A seventh aspect of the present invention is characterized in that the cathode electrode is a copper plate or a platinum plate, the anode electrode is a mesh-shaped stainless-steel net, and the cathode electrode and the anode electrode faces each other. This construction makes it possible to provide an odor sensor that prevents the detection sensitivity from degradation and is fast in reaction rate.

As described below, according to the present invention, it is made possible to provide a biomimetic odor sensor that utilizes neither an oxide semiconductor nor a quartz oscillator, is hardly affected by the atmospheric moisture, in other words, does not need a heater, is simple in structure, inexpensive in production cost, fast in reaction rate, of a wet type, and provided with the condition close to the condition of the nasal mucosa of the human olfactus organ. The use of a biomimetic sensor based on this construction makes it possible to provide a sensor that fast reacts to various odors.

BRIEF DESCRIPTION OF THE DRAWINGS

FIG. 15A is a diagram showing a performance comparison between the odor sensors using β-carotene each based on a dry method and the odor sensors using β-carotene (based on a wet method) of the present invention;

FIG. 15B is a diagram showing a performance comparison between the odor sensors using β-carotene each based on a dry method and the odor sensors using β-carotene (based on a wet method) of the present invention;

FIG. 15C is a diagram showing a performance comparison between the odor sensors using β-carotene each based on a dry method and the odor sensors using β-carotene (based on a wet method) of the present invention;

DESCRIPTION OF SYMBOLS

Figure 1:
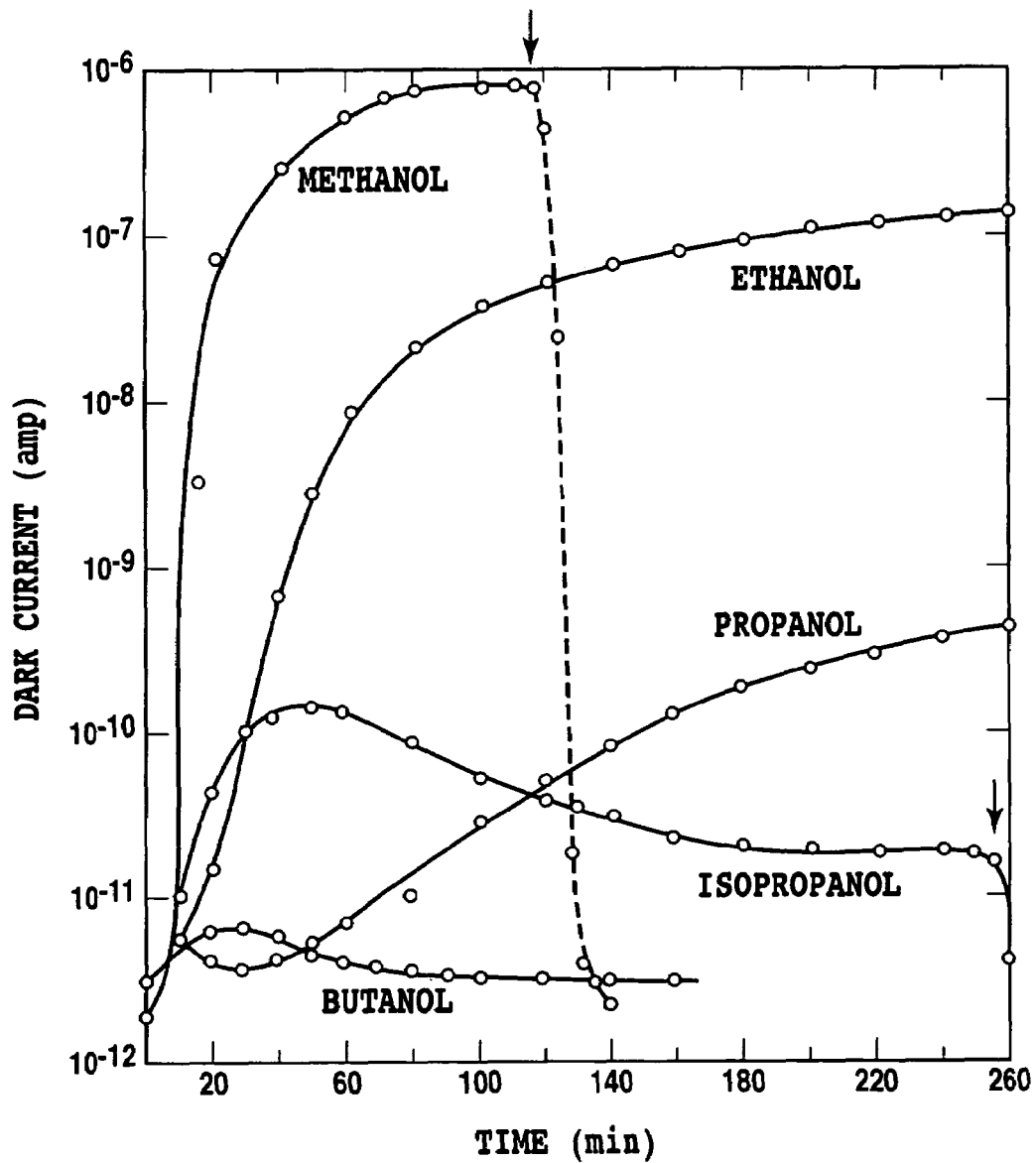
FIG. 1 is a graph showing the response rate of a dry type β-carotene odor sensor that is described by Hiroshi Asai in "Odor Detectors," Solid State Physics (Kotai Butsuri in Japanese), Vol. 10, No. 7, pp. 369-373 (1975)

10 Sensor
12 Mixed material
14 Insulator cover glass (spacer)
16 Copper plate
18 Mesh-shaped stainless-steel (Stainless-steel mesh)
18' Mesh-shaped platinum (Platinum mesh)
20a, 20b Lead wire
30 Sensor
32 Desiccator
34 Constant-voltage generator
36 Digital multi-meter
38 Computer

BEST MODE FOR CARRYING OUT THE INVENTION

Hereinbelow, an embodiment of the present invention is described with reference to the drawings.

Figure 3:
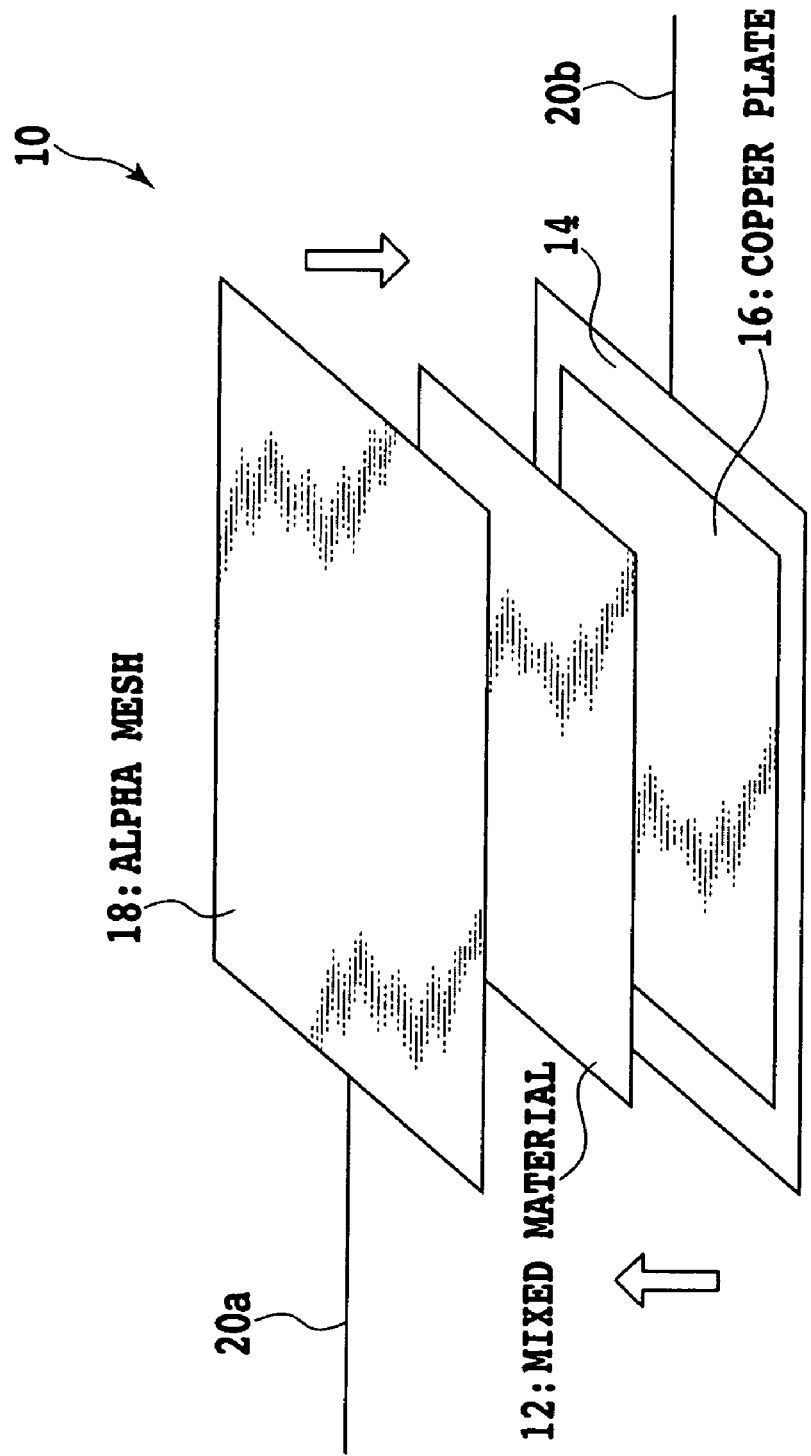
FIG. 3 is a schematic view illustrating the construction of an odor sensor according to an embodiment of the present invention.

FIG. 3 is a schematic view illustrating the construction of a sensor 10 according to an embodiment of the present invention. In the embodiment, the sensor 10 has a structure in which a cathode electrode 16 and an anode electrode 18 are disposed so as to be in contact with a mixed material 12 in which β-carotene and a reducing agent to prevent the oxidation of the β-carotene are dispersed in a viscous liquid.

In the embodiment, the mixed material 12 is cast on a copper plate (or any one of the following metal plates: a platinum plate, a gold plate, a zinc plate, a stainless-steel plate, a nickel plate, and a plate of tin) 16 the periphery of which is covered and surrounded with an insulator cover glass 14, and covered with a fine mesh-shaped stainless-steel mesh (or a metal mesh or a metal porous plate made of any one of platinum, gold, copper, zinc, stainless-steel, nickel and tin) 18. Lead wires 20a and 20b are connected to the copper plate 16 and the stainless-steel mesh 18, respectively. The copper plate 16 and the stainless-steel mesh 18 are disposed so as to face each other, but the arrangement of the copper plate 16 and the stainless-steel mesh 18 is not limited to this arrangement.

Figure 2:
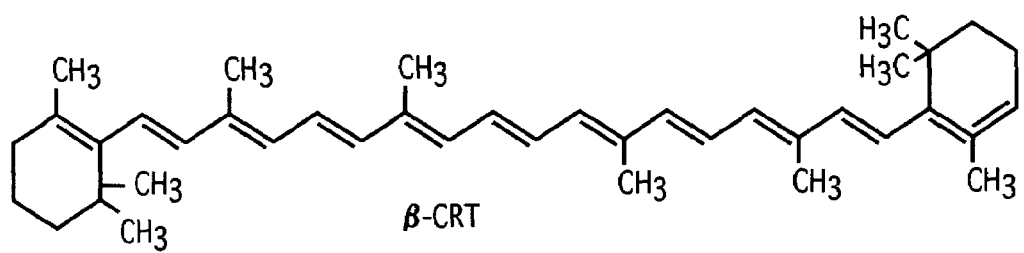
FIG. 2 is a diagram showing a chemical structural formula of β-carotene utilized in the present invention.

FIG. 2 is a diagram showing a chemical structural formula of β-carotene. β-carotene is a very common substance found in all the green plants, and is also found in various internal organs, adipose and olfactus organs of numerous higher animals. In β-carotene, a hydrocarbon chain with double bonds in every other bond forms a line, and a cyclic structure is found at each of the both ends of the line. β-carotene is a substance that has a color of dark purplish red, a melting point of 183° C., and is soluble in benzene, petroleum benzine and chloroform.

The mixed material 12 contains a reducing agent to prevent β-carotene from the oxidation due to the atmospheric oxygen. The mixed material 12 contains, for example, sodium thiosulfate ($Na_2S_2O_3$) as a reducing agent. An alternative example of the reducing agent to prevent the oxidation of β-carotene may be hydro nicotinamide adenine dinucleotide phosphate (NADPH), $Na_2(H_2PO_2)$, L-ascorbic acid or the like.

The use of glycerin and ethanol in the mixed material can lead to realization of a wet type odor sensor that is hardly affected by the atmospheric humidity. The use of ethanol in the mixed material can improve the reaction rate of the sensor.

The viscous liquid is a liquid that is high in viscosity and also high in polarity, and preferably is glycerin having a viscosity of 1.2 Pa·s (pascal·second) (=1200 cP (centipoise)); however, the viscous liquid is not limited to glycerin. It suffices that the viscosity of the mixed material can be modified to fall in a range from 0.1 Pa·s (=100 cP) to 1.5 Pa·s (=1500 cP) with the aid of the ethanol concentration, β-carotene and the reducing agent.

On the basis of the above described construction, it is made possible to provide a biomimetic odor sensor that utilizes neither an oxide semiconductor nor a quartz oscillator, does not utilize a heater, is hardly affected by the atmospheric moisture, simple in structure, inexpensive in production cost, fast in reaction rate, of a wet type, and provided with the condition close to the condition of the nasal mucosa of the human olfactus organ.

EXAMPLE 1

Figure 4:
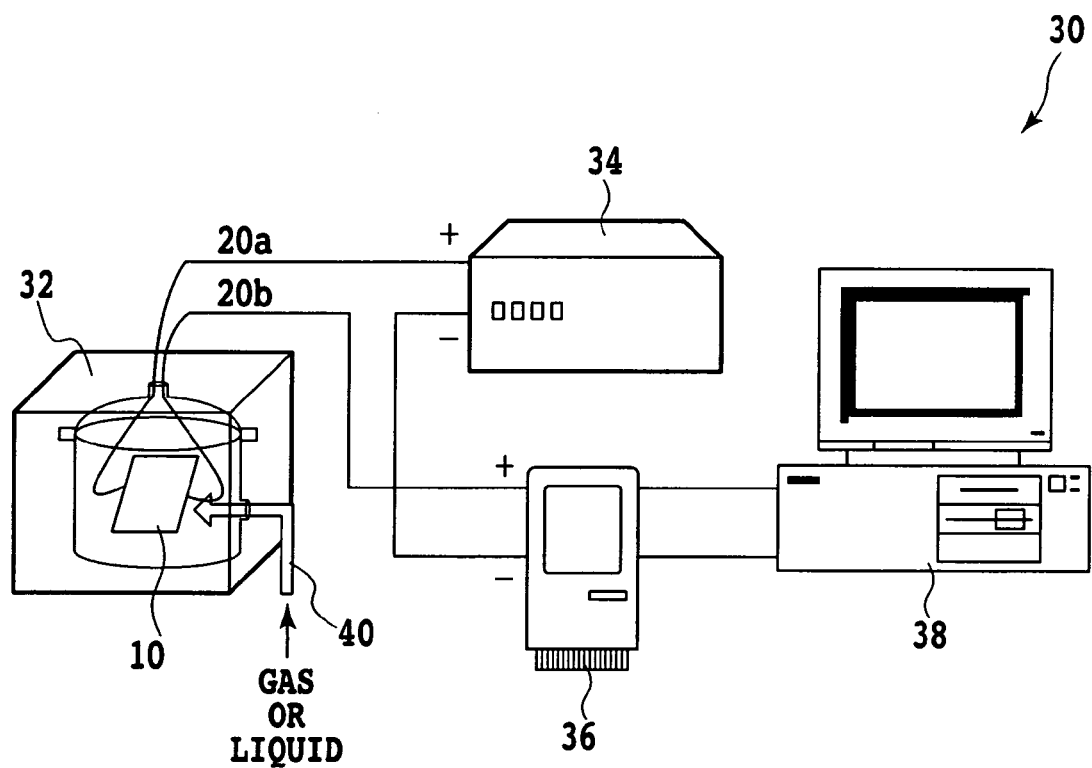
FIG. 4 is a schematic view illustrating the configuration of an odor measurement system using the odor sensor according to the embodiment of the present invention.

FIG. 4 is a schematic view illustrating the configuration of a measurement system to examine the reaction of the above described odor sensor 10 to odors. The sensor 10 is disposed inside a glass desiccator 32. The bottom portion of the glass desiccator 32 is provided with a hose 40 for introducing a liquid containing an odorant to be a target for measurement. The desiccator 32 has a two-storied structure, in which the liquid containing an odorant is disposed in the first floor section, and the sensor 10 is disposed in the second floor section; the desiccator has such an arrangement that does not allow direct contact between the liquid and the sensor 10 other than by diffusion in the air. A lead wire 20b connected to a copper plate 16 of the sensor 10 is connected to a constant-voltage generator 34 through a digital multi-meter 36 in such a way that the copper plate 16 is to serve as a cathode electrode. A lead wire 20a connected to a stainless-steel mesh 18 is connected to the constant-voltage generator 34 in such a way that the stainless-steel mesh 18 is to serve as an anode. A computer 38 is coupled to the digital multi-meter 36 for the purpose of recording the output from the digital multi-meter 36. On the copper plate 16 the periphery of which was covered and surrounded with an insulator cover glass 14 as shown in FIG. 3, there was cast a viscous sol liquid 12 obtained by as a uniform dispersion mixing 112 mg of β-carotene and 9.9 mg of fully pulverized sodium thiosulfate with a mixed solution composed of 5 ml of glycerin and 5 ml of ethanol and sufficiently stirring the solution. The upper side of the thus cast viscous sol liquid 12 was covered with a fine mesh-shaped stainless-steel mesh 18 to form the sensor. A bias of 4 V was applied between the cathode electrode and the anode electrode of the sensor 10.

After the dark current had become stationary, 1 ml of a 45% aqueous ammonia, an odorant, was introduced from outside into the bottom portion of the desiccator by means of the hose 40 beforehand provided to the desiccator.

Figure 5A:
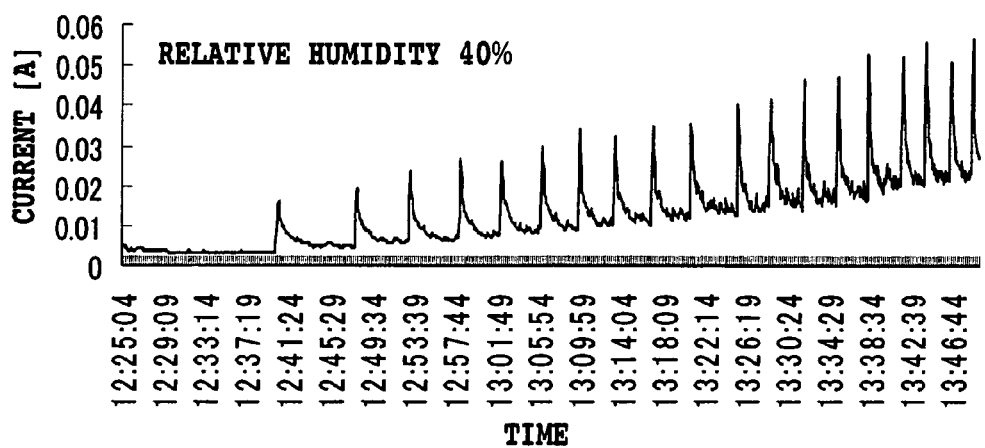
FIG. 5A is a transient current response graph showing the results of the measurement of the odor of ammonia at a relative humidity of 40% with the odor sensor of the present invention.

FIG. 5A is a graph showing the measurement results obtained on a relatively dry day of February in the winter season with a relative humidity of 40%; the introduction time of the aqueous ammonia was 12:38. From after the introduction of the aqueous ammonia, spark-shaped current value variations were observed. This is conceivably ascribable to the repeated cycles of the following reactions: ammonia diffuses in the glycerin solution to be adsorbed on and reacted with β-carotene to form carriers with plus components and carriers with minus components in the glycerin solution, leading to a change in the electric conduction property of the glycerin, and consequently an instantaneous increase in current value is created (the carriers travel) and then the current value again gets back to the dark current value. The peak current generated by the odor is about 18 mA. The rise time, the fall time and the reaction rate (response onset time) of the repeated pulses are 5 seconds, 5 seconds and less than 1 minute (for example, 40 seconds), respectively.

Figure 5B:
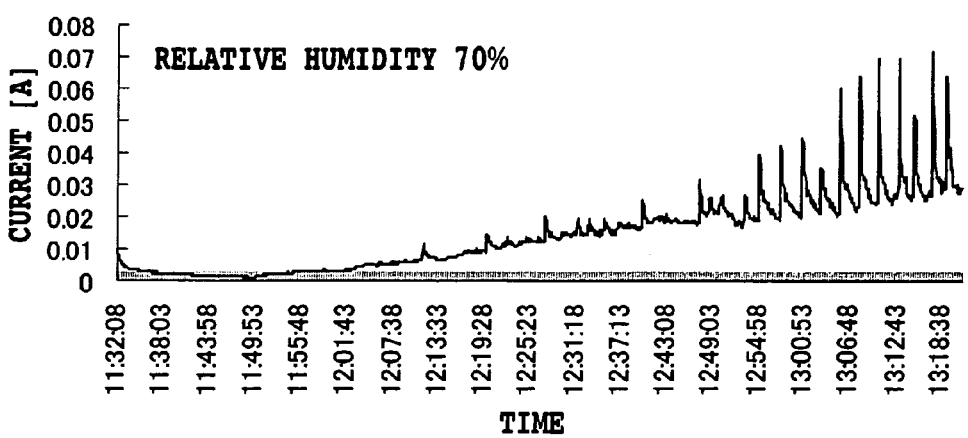
FIG. 5B is a transient current response graph showing the results of the measurement of the odor of ammonia at a relative humidity of 70% with the odor sensor of the present invention.

FIG. 5B is a graph showing the measurement results obtained on a day after a rain with a relative humidity of 70%. Pulses similar to those in FIG. 5A were observed, and it can be seen that the odor sensor of the present invention exhibits a satisfactory response to odor independently of the humidity conditions.

The introduction time of ammonia was 12:00, and before the introduction, absolutely no current generation was identified, so that it can be seen that the individual pulse-shaped peak currents were the response currents due to the reaction to the odorant. When a platinum plate was used in place of the copper plate, the current values were increased by a factor of a few tens to reach a few hundreds mA. This type of phenomenon was also observed for the case where a gold plate was used in place of the copper plate. Any one of the metal plates such as a zinc plate, a stainless-steel plate, a nickel plate and a plate of tin can be used in place of the copper plate; however, from the viewpoints of the life and stability of the sensor, a platinum plate or a gold plate is effective.

EXAMPLE 2

Figure 6:
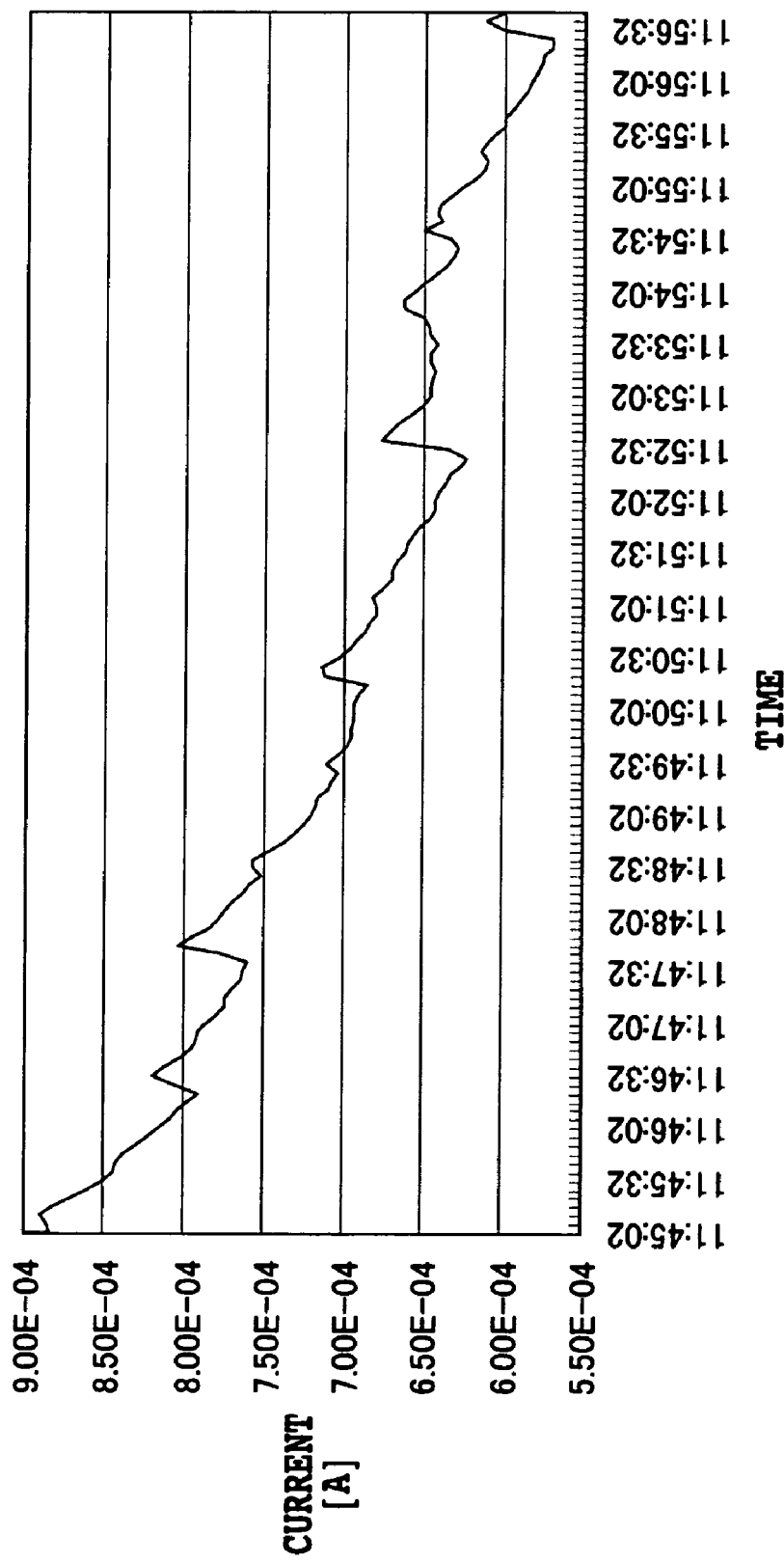
FIG. 6 is a transient current response graph showing the results of the measurement of the odor of trimethylamine with the odor sensor of the present invention.

FIG. 6 is a graph showing the response of the same sensor 10 as in Example 1 to an odorant, namely, trimethylamine. The same measurement system configuration as in Example 1 was used except that: 1 ml of trimethylamine, an odorant, was placed in a 5 cc weighing bottle in such an arrangement that the bottle was closed with the cap, the cap was attached with a piece of string so that the cap might be taken off by pulling the piece of string from the outside; and the weighing bottle was placed inside the glass desiccator 32 shown in FIG. 4. A bias of 4 V was applied.

After the dark current had become stationary, the cap of the weighing bottle was taken off by pulling the piece of string from the outside, trimethylamine, an odorant, was introduced inside the desiccator. In the same manner as in Example 1, the odor sensor and trimethylamine, an odorant, were not allowed to be in direct contact with each other than by diffusion in the air. The time of the introduction of trimethylamine was 11:45.

After the introduction of trimethylamine, the current value variation as shown in FIG. 6 was observed. This is conceivably ascribable to the repeated cycles of the following reactions: trimethylamine diffuses in the glycerin solution to be adsorbed on and reacted with β-carotene to form carriers with plus components and carriers with minus components in the glycerin, leading to a change in the electric conduction property of the glycerin, and consequently a slow increase in current value is created (the carriers travel) and then the current value again gets back to the dark current value.

The peak current generated by the odor is about 50 μA. The rise time, the fall time and the response rate of the repeated pulses are 10 seconds, 40 seconds and 2 minutes, respectively.

EXAMPLE 3

Figure 7:
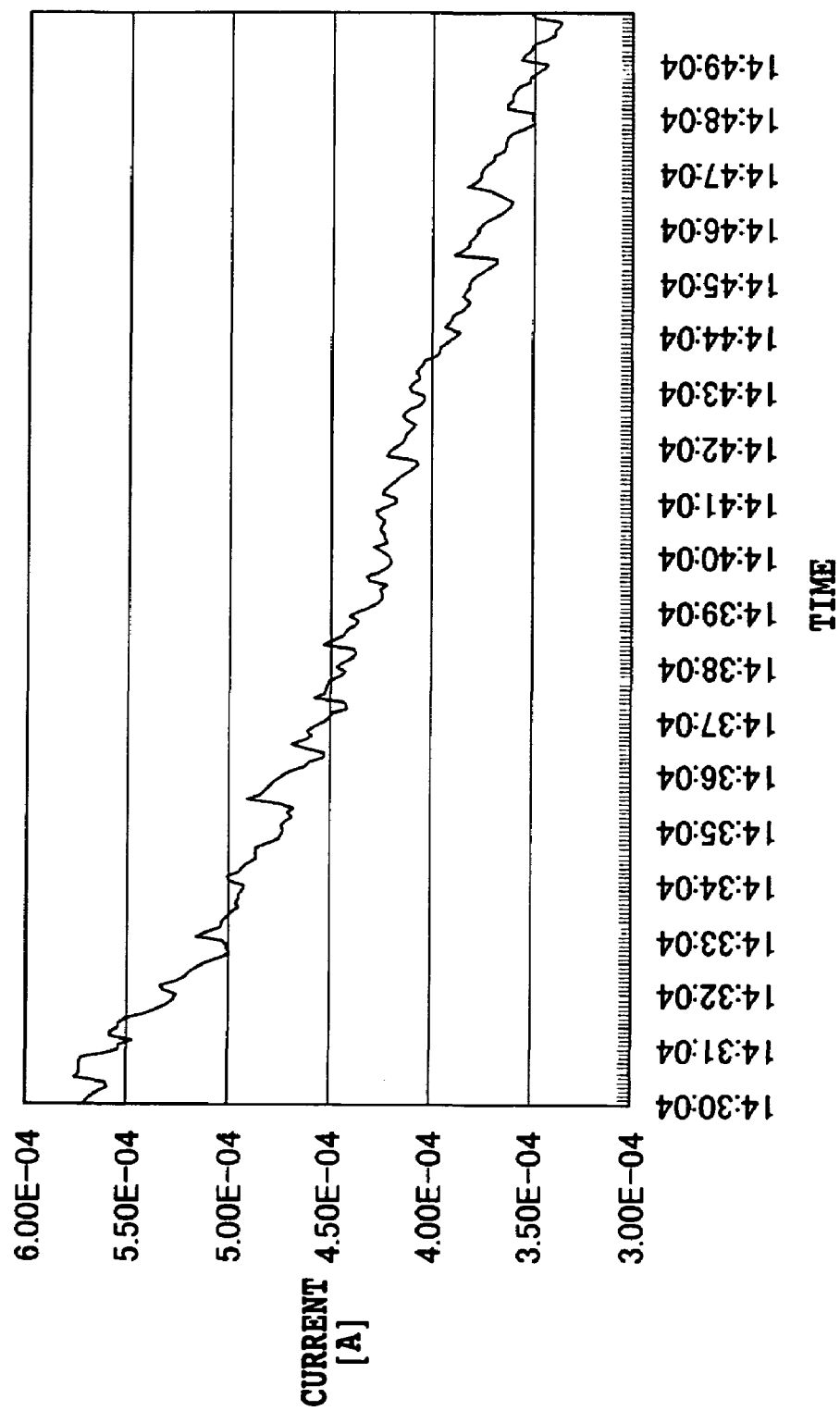
FIG. 7 is a transient current response graph showing the results of the measurement of the odor of butanol with the odor sensor of the present invention.

FIG. 7 is a graph showing the response of the same sensor 10 as in Example 1 to an odorant, namely, butanol. In the same manner as in Example 2, 1 ml of butanol, an odorant, was placed in a 5 cc weighing bottle in such an arrangement that the bottle was closed with the cap, the cap was attached with a piece of string so that the cap might be taken off by pulling the piece of string from the outside, and the weighing bottle was placed inside the glass desiccator 32. The sensor was applied with the same bias of 4 V as in Examples 1 and 2.

After the dark current had become stationary, the cap of the weighing bottle was taken off by pulling the piece of string from the outside, butanol, an odorant, was introduced inside the desiccator. The time of the introduction of butanol was 14:30. The odor sensor and butanol, an odorant, were not allowed to be in direct contact with each other than by diffusion in the air.

After the introduction of butanol, the current value variation as shown in FIG. 7 was observed. This is conceivably ascribable to the repeated cycles of the following reactions: butanol diffuses in the glycerin solution to be adsorbed on and reacted with β-carotene to cause a change in the electric conduction property of the glycerin solution, and consequently a slow increase in current value is created (the carriers travel) and then the current value again gets back to the dark current value.

The peak current generated by the odor is about 20 μA. The rise time, the fall time and the response rate of the repeated pulses are 10 seconds, 50 seconds and 40 seconds, respectively.

EXAMPLE 4

Figure 8:
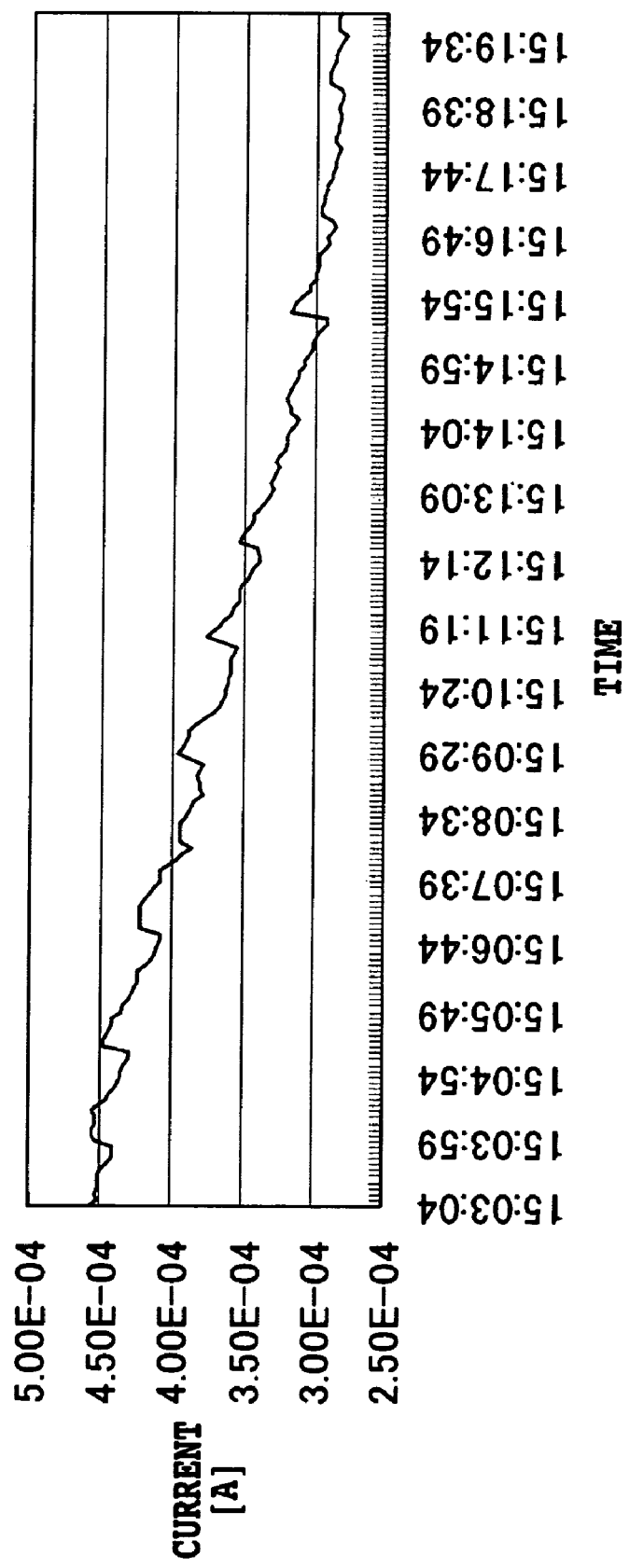
FIG. 8 is a transient current response graph showing the results of the measurement of the odor of propanol with the odor sensor of the present invention.

In Example 4, description is made on the following sensor 10 prepared as follows: on a platinum plate the periphery of which was covered and surrounded with an insulator cover glass as shown in FIG. 3, there was cast a viscous sol liquid obtained as a uniform dispersion by mixing 112 mg of β-carotene and 1 mg of hydro nicotinamide adenine dinucleotide phosphate (NADPH) with a mixed solution composed of 5 ml of glycerin and 5 ml of ethanol, and the solution was sufficiently stirring the solution. The upper side of the thus cast viscous sol liquid was covered with a fine mesh-shaped stainless-steel net to form the sensor 10. FIG. 8 is a graph showing the response of the sensor 10 of Example 4 to propanol, an odorant. In the same manner as in Examples 2 and 3, 1 ml of propanol, an odorant, was placed in a 5 cc weighing bottle in such an arrangement that the bottle was closed with the cap, the cap was attached with a piece of string so that the cap might be taken off by pulling the piece of string from the outside, and the weighing bottle was placed inside the glass desiccator 32 shown in FIG. 4. A lead wire 20b connected to the platinum plate is connected to a constant-voltage generator 34 through a digital multi-meter 36 in such a way that the platinum plate is to serve as a cathode electrode. A lead wire 20a connected to the stainless-steel mesh 18 is connected to the constant-voltage generator 34 in such a way that the stainless-steel mesh 18 is to serve as an anode. In the same manner as in Example 1, a personal computer is coupled to the digital multi-meter. A bias of 4 V was applied to the sensor 10.

After the dark current had become stationary, the cap of the weighing bottle was taken off by pulling the piece of string from the outside, propanol, an odorant, was introduced inside the desiccator. In the same manner as in Examples 1 to 3, the odor sensor and propanol, an odorant, were not allowed to be in direct contact with each other other than by diffusion in the air. The time of the introduction of propanol was 14:48.

After the introduction of propanol, the current value variation as shown in FIG. 8 was observed. This is conceivably ascribable to the repeated cycles of the following reactions: propanol diffuses in the glycerin solution to be adsorbed on and reacted with β-carotene to cause a change in the electric conduction property of the glycerin solution, and consequently a slow increase in current value is created (the carriers travel) and then the current value again gets back to the dark current value. The peak current generated by the odor was 133 μA. The rise time, the fall time and the response rate of the repeated pulses are 10 seconds, 45 seconds, and 15 minutes 14 seconds, respectively.

EXAMPLE 5

Figure 9:
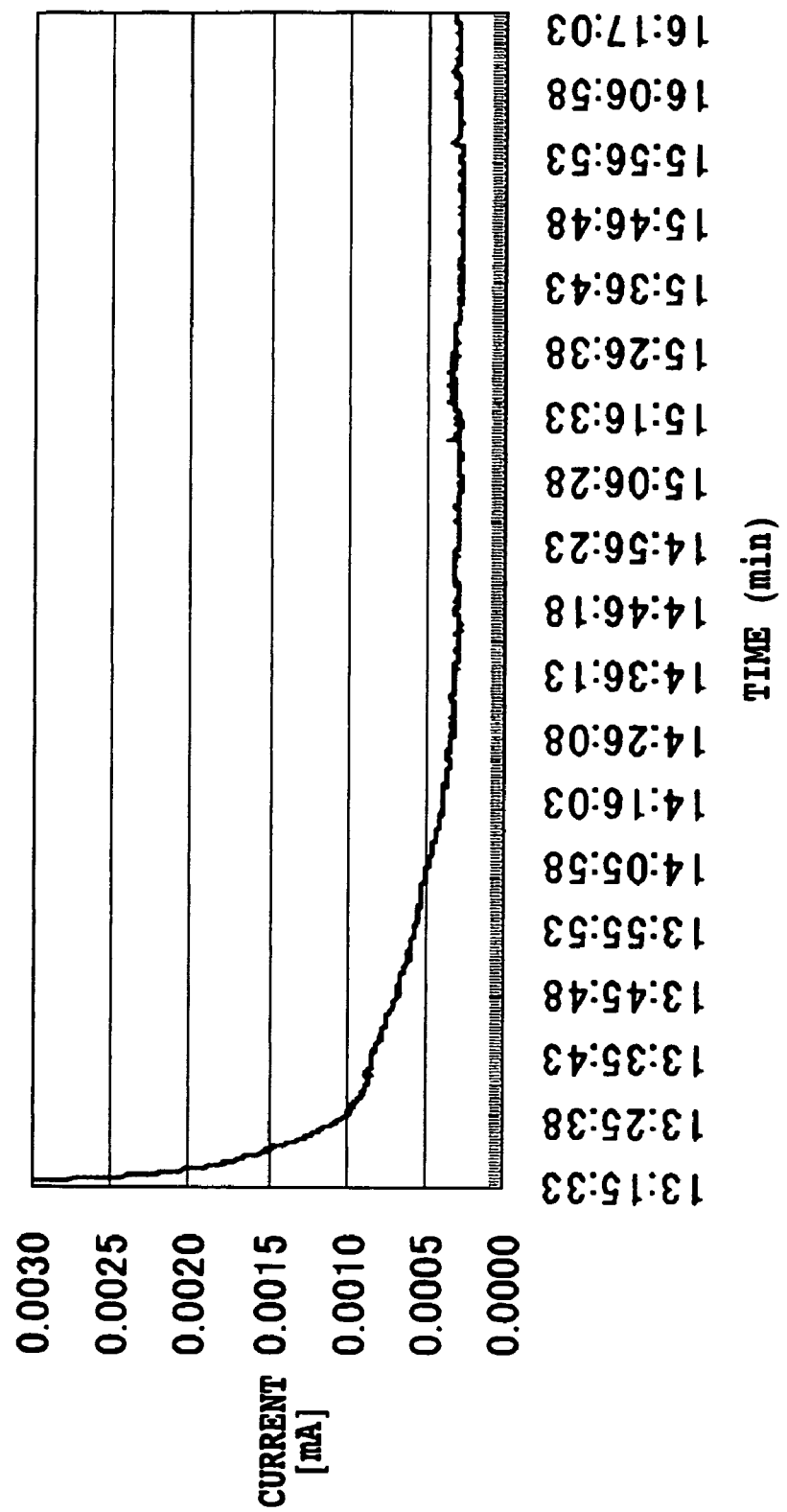
FIG. 9 is a transient current response graph showing the results of the measurement of the odor of 2-phenylethanol with the odor sensor of the present invention.

FIG. 9 shows the results obtained by studying the reaction to 2-phenyl ethanol with the same measurement system as in Example 1. The time of the introduction of 2-phenyl ethanol was 13:20. The response rate was 2 minutes 55 seconds. The peak current was 1.62 mA.

EXAMPLE 6

Figure 10:
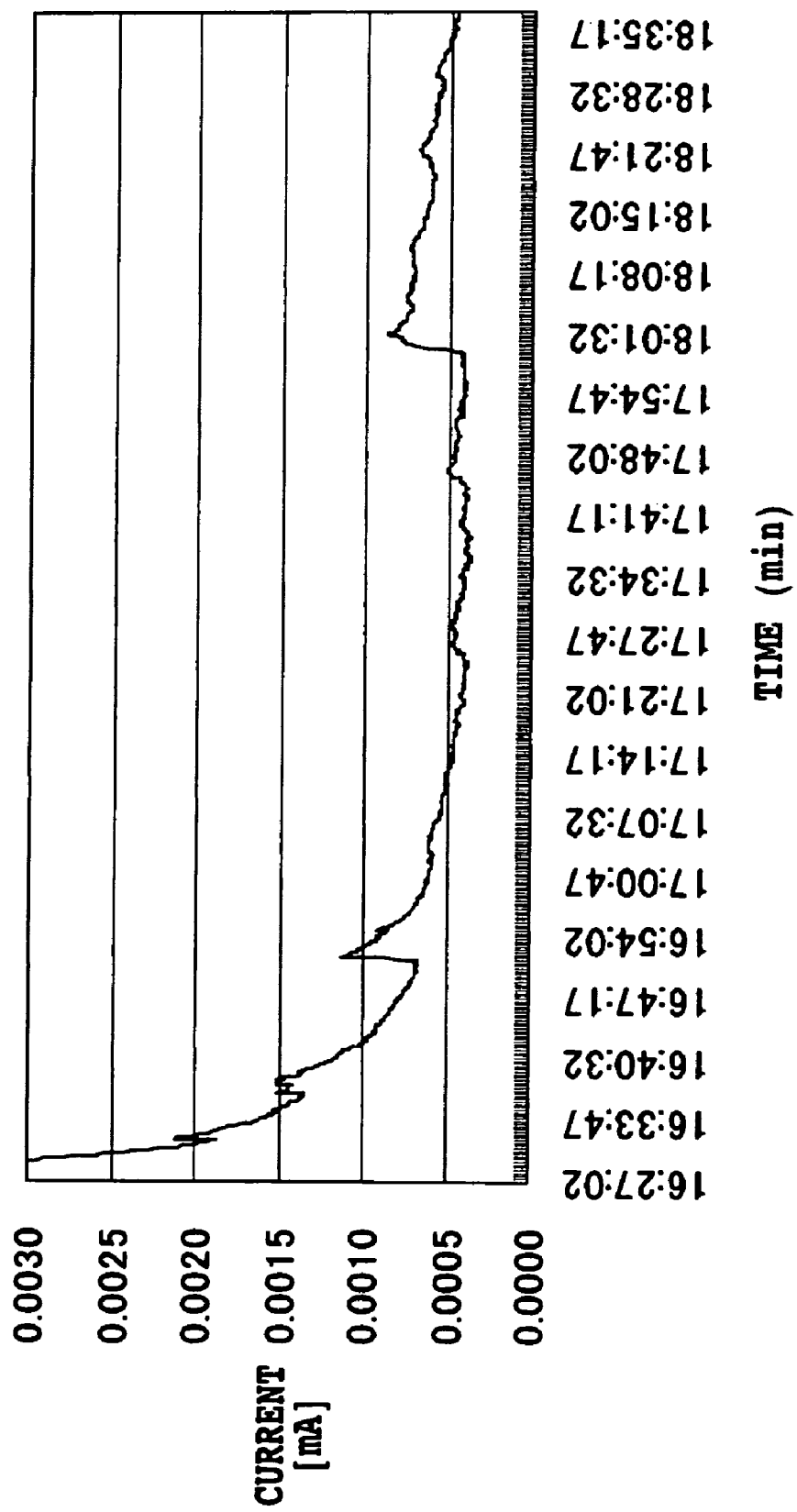
FIG. 10 is a transient current response graph showing the results of the measurement of the odor of geraniol with the odor sensor of the present invention.

FIG. 10 shows the results obtained by studying the reaction to geraniol with the same measurement system as in Example 1. The time of the introduction of geraniol was 16:46. The response rate was 5 minutes 37 seconds. The peak current was 85 μA.

EXAMPLE 7

Figure 11:
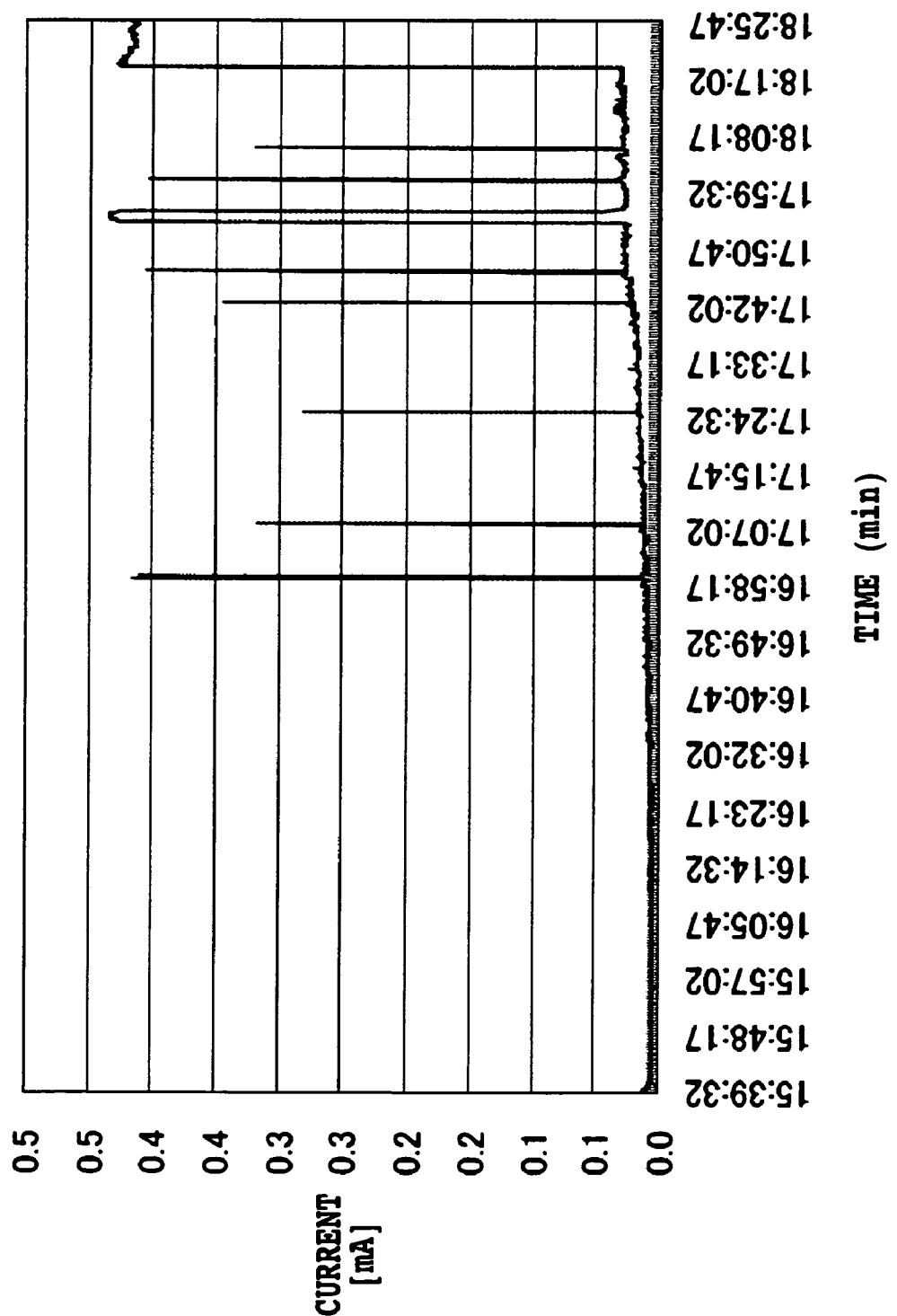
FIG. 11 is a transient current response graph showing the results of the measurement of the odor of ammonia with an odor sensor in which the copper plate 16 in FIG. 3 is replaced with a platinum plate.

FIG. 11 shows the results obtained by studying the reaction to ammonia with the measurement system in Example 1 that has platinum plate of taking the place of copper plate 16. The time of the introduction of ammonia was 16:57. The response rate was 55 seconds. The peak current was 300 mA.

EXAMPLE 8

Figure 12C:
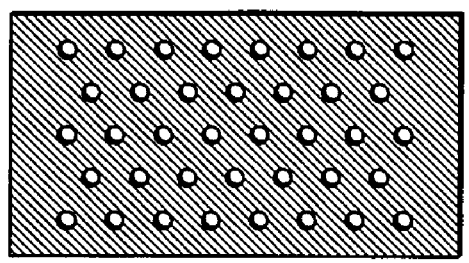
FIG. 12C is a view illustrating yet another example of the shape of the glass cover 14 shown in FIG. 3.
Figure 12B:
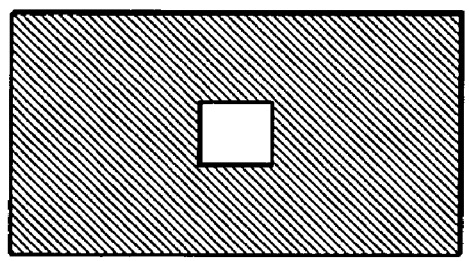
FIG. 12B is a view illustrating another example of the shape of the glass cover 14 shown in FIG. 3.
Figure 12A:
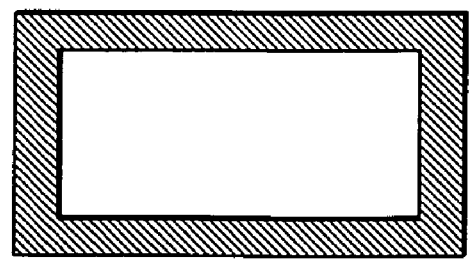
FIG. 12A is a view illustrating an example of a shape of a glass cover 14 shown in FIG. 3.

FIGS. 12A, 12B and 12C show examples of the shape of the insulator cover glass 14 shown in FIG. 3. The insulator is provided to prevent the contact between the cathode electrode and the anode electrode disposed so as to be in contact with the mixed material. The insulator is also referred to as a spacer in the present specification. The window formed in the spacer shown in FIG. 12A amounts in size to 29.0% of the whole spacer. The window formed in the spacer shown in FIG. 12B amounts in size to 6.5% of the whole spacer. The windows formed in the spacer shown in FIG. 12C collectively amount in size to 3.1% of the whole spacer.

Figure 13A:
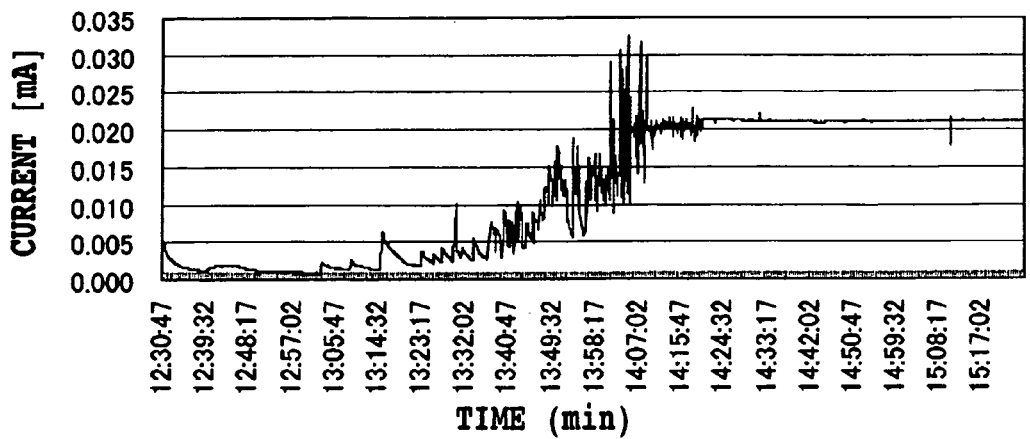
FIG. 13A is a transient current response graph showing the results of the measurement of the odor of ammonia with an odor sensor in which the glass cover 14 in FIG. 3 is replaced with a spacer shown in FIG. 12A.
Figure 13B:
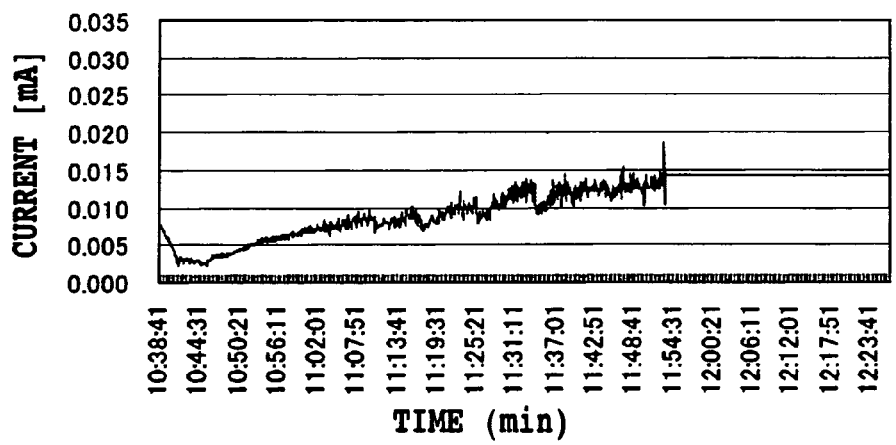
FIG. 13B is a transient current response graph showing the results of the measurement of the odor of ammonia with an odor sensor in which the glass cover 14 in FIG. 3 is replaced with a spacer shown in FIG. 12B.
Figure 13C:
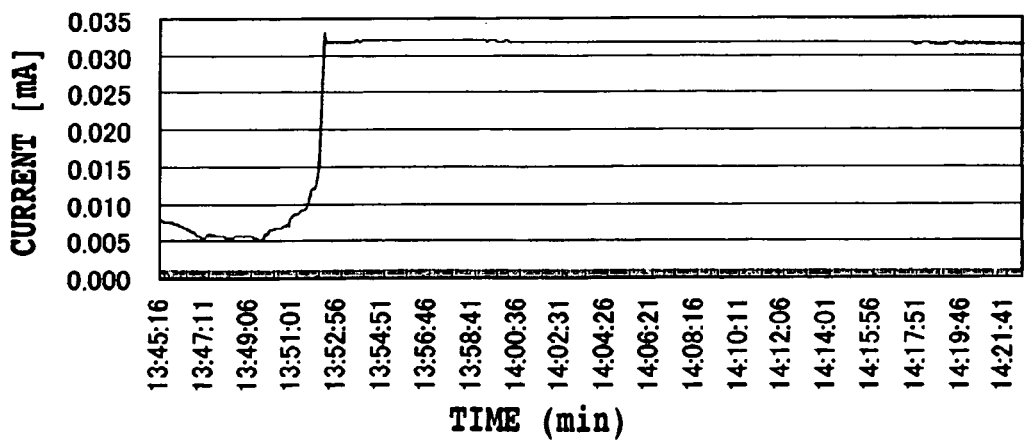
FIG. 13C is a transient current response graph showing the results of the measurement of the odor of ammonia with an odor sensor in which the glass cover 14 in FIG. 3 is replaced with a spacer shown in FIG. 12C.

FIGS. 13A, 13B and 13C show the results obtained by studying the reaction to ammonia, by use of the odor sensors respectively using the spacers shown in FIGS. 12A, 12B and 12C, with the measurement system configuration used in Example 1.

EXAMPLE 9

Figure 14:
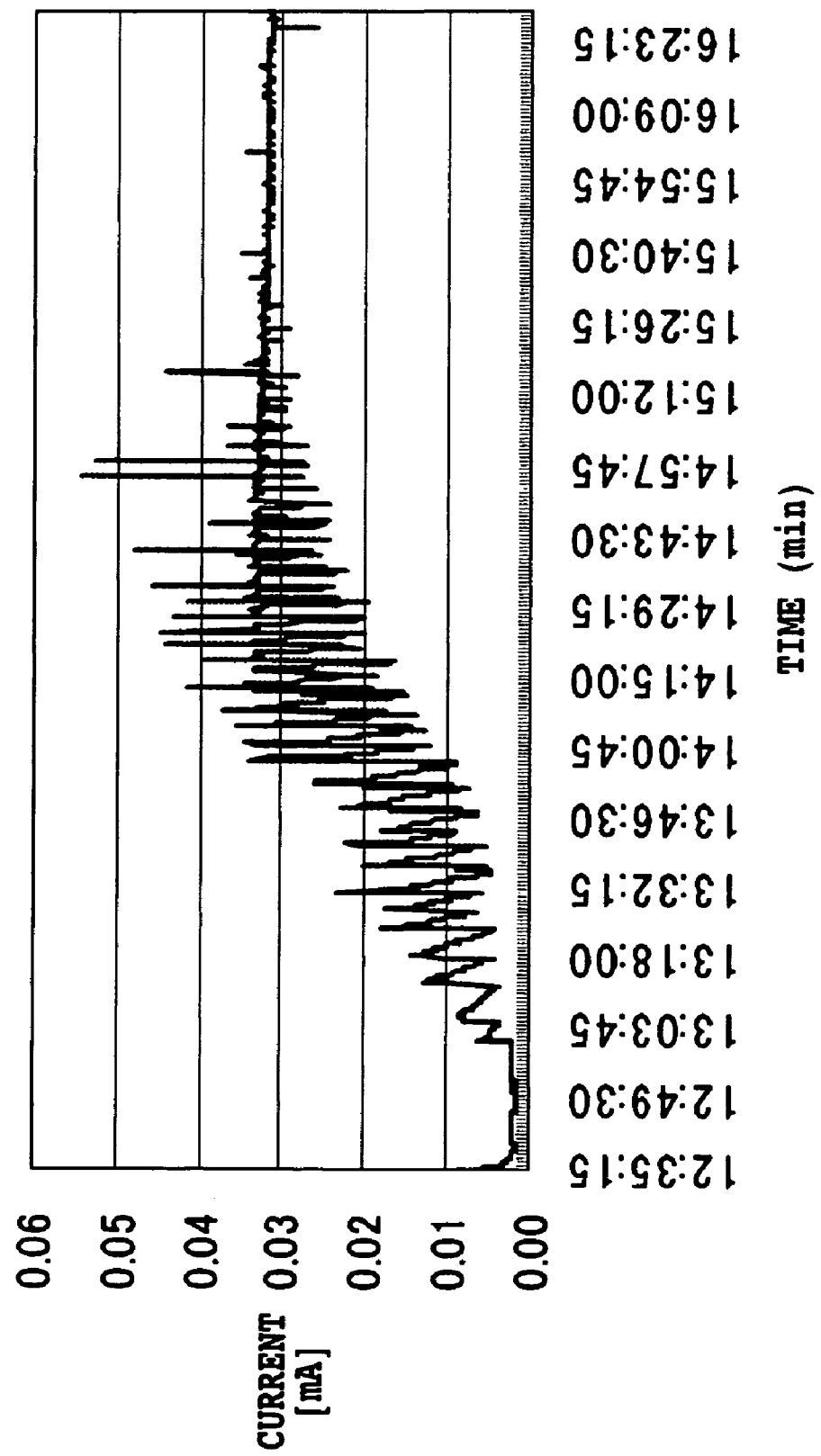
FIG. 14 is a transient current response graph showing the results of the measurement of the odor of ammonia in a place without a light with the odor sensor shown in FIG. 3.

FIG. 14 shows the results obtained by studying the response to ammonia in a place without light with the measurement system configuration shown in Example 1. It can be seen that the odor sensor of the present invention is better in response in a place without light than under illumination (FIG. 5A). Additionally, the life of the odor sensor is shortened under illumination, and accordingly, the odor sensor is preferably to be used in a place without light.

EXAMPLE 10

A life measurement experiment was carried out for each of an odor sensor using a stainless-steel mesh 18 and an odor sensor using a platinum mesh 18'. The conditions of the life measurement experiment are the same as those shown in Example 1 except that the odor sensors were different in the alpha mesh material from each other. It is to be noted that when the platinum mesh 18' was used, a platinum plate was used as the counter electrode to the platinum mesh 18'. In each of the life measurement experiments, 1 ml of a 45% aqueous ammonia was added at 10 a.m. and at 3 p.m. every day, and the responses of each of the odor sensors were studied. With the odor sensor using the stainless-steel mesh 18, no response was found in 1 week. With the odor sensor using the platinum mesh 18', the response continued for 1 month or more.

FIGS. 15A, 15B and 15C summarize: the reactions to methanol of conventional sensors each with electrodes sandwiching a powder of β-carotene therebetween; the reactions to the individual odorants in the present invention, shown in the above described examples; and the reactions to other odorants of an odor sensor of the present invention.

As shown in FIGS. 15A, 15B and 15C, the odor sensors of the present invention are larger by a factor of about 60 in response rate and by a factor of about 1000 in response ability than the conventional sensors each with electrodes sandwiching a powder of β-carotene therebetween. The odor sensors of the present invention are in variance in their response onset times, peak currents and others, but can react to various odors.

Figure 16:
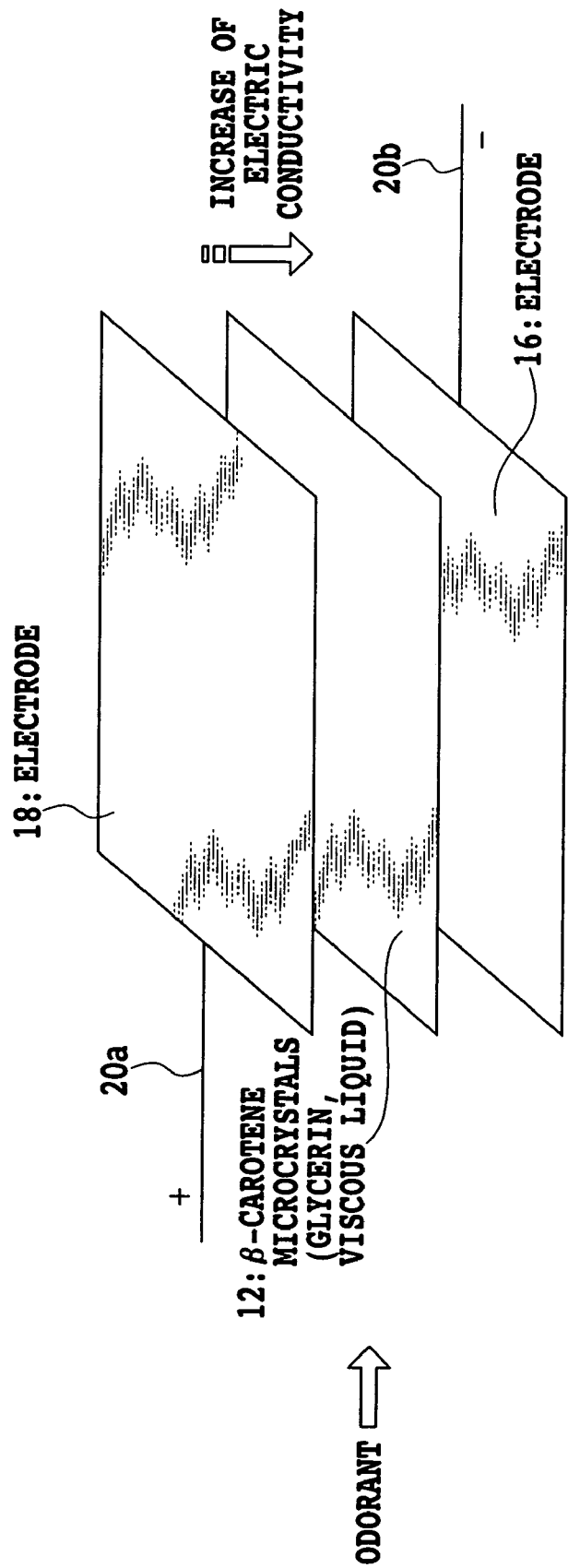
FIG. 16 is a diagram illustrating the sensor response principle of the odor sensor (based on a wet method) of the present invention.
Figure 17:
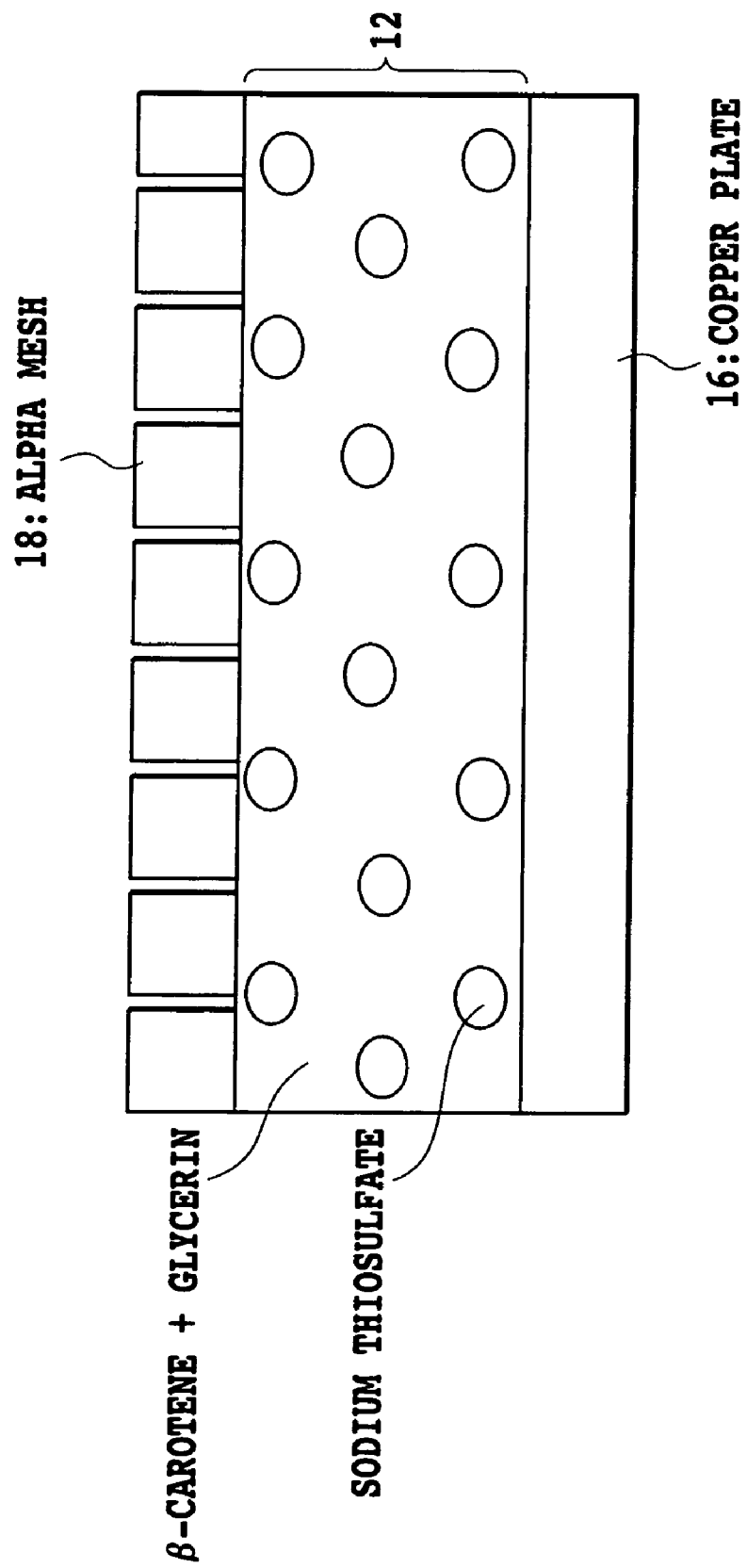
FIG. 17 is an enlarged schematic diagram illustrating the odor sensor (based on a wet method) of the present invention.

As shown in FIG. 16, the principle of the odor sensor according to the present invention is conceivable that an odorant is adsorbed on and reacts with β-carotene to cause the electric conduction property variation which results in the current response variation to be detected, similar to a conventional sensor in which a microcrystalline powder of β-carotene is sandwiched between electrodes. The difference between the odor sensor according to the present invention and the conventional sensor in which a microcrystalline powder of β-carotene is sandwiched with electrodes resides in that as shown in FIG. 17, the odor sensor according to the present invention is provided with a mixed material in which β-carotene and sodium thiosulfate, for example, as a reducing agent to prevent the oxidation of the β-carotene are dispersed in a viscous liquid such as glycerin. In other words, the conventional odor sensor in which a microcrystalline powder of β-carotene is sandwiched with electrodes is of a dry type, but the sensor according to present invention is of a wet type. Specifically, the dry type sensor based on the conventional method is slow in reaction rate because of the solid phase reactions involved, but the odor sensor according to the present invention is of a wet type, accordingly involves liquid phase reactions in a viscous liquid similarly in the human olfactory cell enveloped by mucosa, and consequently can provide an odor sensor that has a relatively fast response property and an efficient response (a high response current) property.

The invention claimed is:

1. An odor sensor in which the electric conductivity thereof is varied in response to odor, the odor sensor including:
   a mixed material in which β-carotene and a reducing agent to prevent the oxidation of the β-carotene are dispersed in a viscous liquid, wherein the reducing agent is any of sodium thiosulfate($Na_2S_2O_3$), hydro nicotinamide adenine dinucleotide phosphate (NADPH), Na2(H2PO2) and L-ascorbic acid and the viscous liquid is a liquid with high viscosity and polarity; and
   a cathode electrode and an anode electrode that are disposed so as to be in contact with the mixed material,
   wherein odor of an odorant is detected when the β-carotene in the mixed material absorbs and reacts with the odorant causing electric conduction property variation between the cathode electrode and the anode electrode.

2. The odor sensor according to claim 1, wherein the liquid with high viscosity and polarity is glycerin.

3. The odor sensor according to claim 1, wherein ethanol is further mixed as a viscosity modifier.

4. The odor sensor according to claim 1 having a structure in which the mixed material is sandwiched with the cathode electrode and the anode electrode facing each other.

5. The odor sensor according to claim 1, wherein:
   the cathode electrode is a copper plate or a platinum plate;
   the anode electrode is a mesh-shaped stainless-steel net; and
   the cathode electrode and the anode electrode face each other.

6. The odor sensor according to claim 1, wherein:
   the cathode electrode is a copper plate or a platinum plate;
   the anode electrode is a mesh-shaped platinum net; and
   the cathode electrode and the anode electrode face each other.

7. An odor sensor in which the electric conductivity thereof is varied in response to odor, the odor sensor comprising:
   a mixed material including β-carotene and a reducing agent dispersed in a viscous liquid, the reducing agent preventing the oxidation of the β-carotene, wherein the reducing agent is at least one of sodium thiosulfate($Na_2S_2O_3$), hydro nicotinamide adenine dinucleotide phosphate (NADPH), Na2(H2PO2) and L-ascorbic acid; and
   a cathode electrode and an anode electrode disposed to be in contact with the mixed material,
   wherein odor of an odorant is detected when the β-carotene in the mixed material absorbs and reacts with the odorant causing electric conduction property variation between the cathode electrode and the anode electrode.

8. An odor sensor in which the electric conductivity thereof is varied in response to odor, the odor sensor comprising:
   a mixed material including β-carotene and a reducing agent dispersed in a viscous liquid, the reducing agent preventing the oxidation of the β-carotene, wherein the viscous liquid is a liquid with high viscosity and polarity; and
   a cathode electrode and an anode electrode disposed to be in contact with the mixed material,
   wherein odor of an odorant is detected when the β-carotene in the mixed material absorbs and reacts with the odorant causing electric conduction property variation between the cathode electrode and the anode electrode.

9. A method of detecting odor performed by an odor sensor that varies electric conductivity in response to odor, the method comprising:
   dispersing β-carotene and a reducing agent in a viscous liquid, the reducing agent preventing the oxidation of the β-carotene, wherein the viscous liquid is a liquid with high viscosity and polarity;
   disposing a cathode electrode and an anode electrode such that the cathode electrode and the anode electrode are in contact with said dispersed viscous liquid; and
   detecting odor of an odorant when the β-carotene absorbs and reacts with the odorant to cause electric conduction property variation between the cathode electrode and the anode electrode.

10. A method of detecting odor performed by an odor sensor that varies electric conductivity in response to odor, the method comprising:
    dispersing β-carotene and a reducing agent in a viscous liquid, the reducing agent preventing the oxidation of the β-carotene, wherein the reducing agent is at least one of sodium thiosulfate($Na_2S_2O_3$), hydro nicotinamide adenine dinucleotide phosphate (NADPH), Na2(H2PO2) and L-ascorbic acid;
    disposing a cathode electrode and an anode electrode such that the cathode electrode and the anode electrode are in contact with said dispersed viscous liquid; and
    detecting odor of an odorant when the β-carotene absorbs and reacts with the odorant to cause electric conduction property variation between the cathode electrode and the anode electrode.

11. The odor detecting method according to claim 10, wherein the viscous liquid is a liquid with high viscosity and polarity.

* * * * *